(12) United States Patent
Seitz, Jr. et al.

(10) Patent No.: US 8,353,965 B2
(45) Date of Patent: Jan. 15, 2013

(54) SMALL JOINT ORTHOPEDIC IMPLANTS AND THEIR MANUFACTURE

(76) Inventors: William H. Seitz, Jr., Shaker Heights, OH (US); Albert N. Santilli, Pepper Pike, OH (US)

( * ) Notice: Subject to any disclaimer, the term of this patent is extended or adjusted under 35 U.S.C. 154(b) by 1032 days.

(21) Appl. No.: 11/162,258

(22) Filed: Sep. 2, 2005

(65) Prior Publication Data
US 2006/0052725 A1    Mar. 9, 2006

Related U.S. Application Data

(60) Provisional application No. 60/607,473, filed on Sep. 3, 2004.

(51) Int. Cl.
*A61F 2/30* (2006.01)

(52) U.S. Cl. ..................... 623/23.44; 623/901

(58) Field of Classification Search .... 623/20.11–20.13, 623/18.11, 20.34, 21.12, 21.15, 21.18, 23.21, 623/23.44, 23.14, 23.24, 23.32, 23.15, 23.46, 623/20.36, 22.43, 23.25, 23.48; 600/443
See application file for complete search history.

(56) References Cited

U.S. PATENT DOCUMENTS

| | | | |
|---|---|---|---|
| 2,934,065 A * | 4/1960 | Townley | 623/23.14 |
| 3,728,742 A | 4/1973 | Averill et al. | |
| 3,987,500 A * | 10/1976 | Schlein | 623/21.18 |
| 4,180,871 A | 1/1980 | Hamas | |
| 4,506,393 A * | 3/1985 | Murphy | 600/425 |
| 4,704,686 A | 11/1987 | Aldinger | |
| 4,783,192 A * | 11/1988 | Wroblewski et al. | 623/23.21 |
| 4,936,862 A | 6/1990 | Walker et al. | |
| 4,946,379 A * | 8/1990 | Berchem | 623/23.44 |
| 5,002,579 A | 3/1991 | Copf et al. | |

(Continued)

FOREIGN PATENT DOCUMENTS
WO    WO 9200045 A1 *    1/1992

OTHER PUBLICATIONS

"Outcomes", Cleveland Orthop[aedic and Spine Hospital, Lutheran Hospital, 2004.*

(Continued)

*Primary Examiner* — Brian Pellegrino
(74) *Attorney, Agent, or Firm* — Wayne D. Porter, Jr.

(57) ABSTRACT

A technique to manufacture small joint orthopedic implants includes the steps of taking standard radiographs of a pathologic joint and the corresponding non-pathologic joint. In order to provide an accurate frame of reference, a specialized marker is placed in the radiographic field. By inspection of the radiographs and by comparison with the marker, the dimensions of the cortical bone and the cancellous bone can be quickly and accurately determined. These dimensions can be used to manufacture a suitable implant and installation tool. Typically, the implant will include a stem from which a post projects. A radially extending collar is located at the intersection between the stem and the post. A mating head is attached to the post. The head closely approximates the size and shape of the natural head being replaced. The stem will be non-round in cross-section to prevent rotation of the stem in the bone. For many applications, the head will not be fixedly attached to the post, but will be rotatable about the longitudinal axis of the post. One or more spacers that fit about the stem also can be provided in order to adjust the distance that the head projects from the bone.

22 Claims, 2 Drawing Sheets

U.S. PATENT DOCUMENTS

| | | | |
|---|---|---|---|
| 5,030,237 | A | 7/1991 | Sorbie et al. |
| 5,116,380 | A * | 5/1992 | Hewka et al. .............. 623/23.25 |
| 5,326,366 | A | 7/1994 | Pascaralla et al. |
| 5,522,900 | A | 6/1996 | Hollister |
| 5,549,690 | A | 8/1996 | Hollister et al. |
| 5,591,604 | A | 1/1997 | Fuchs et al. |
| 6,361,563 | B2 | 3/2002 | Terrill-Grisoni |
| 6,709,459 | B1 * | 3/2004 | Cooney et al. ............. 623/20.11 |
| 6,932,842 | B1 * | 8/2005 | Litschko et al. .............. 623/901 |
| 2003/0060883 | A1 | 3/2003 | Fell et al. |
| 2003/0120276 | A1 | 6/2003 | Tallarida et al. |
| 2008/0183104 | A1 * | 7/2008 | Tuma et al. .................. 600/587 |

OTHER PUBLICATIONS

American Society for Surgery of the Hand, Industry Sponsored Workshops, May 5, 2004.*

"The Seitz Solution", Kapp Surgical Instrument, INC, date unknown.*

Gupta et al, "Custom Radial Head Prosthetic Replacement" Sep. 30, 2004.*

Swanson Titanium Radial Head Implant, Wright Medical Technology, Publication No. SO 378-995, Rev. No. 0402.

Swanson Basal Thumb Implant, Wright Medical Technology, Publication No. SO 232-1187, Rev. No. 1002.

"2003—New Technology in Upper Extremity Surgery: The Cutting Edge," Cleveland Orthopaedic and Spine Hospital at Lutheran, Jul. 11, 2003.

"Custom Radial Head Prosthetic Replacement The 'Bioclone' Radial Head Custom Implant," Cleveland Orthopaedic and Spine Hospital at Lutheran, Nov. 2003.

Sietz, William H., Jr., Custom Radial and Ulnar Head Prosthetic Replacement, Nov. 2003.

"2004—New Technology in Upper Extremity Surgery: The Cutting Edge," Cleveland Orthopaedic and Spine Hospital at Lutheran, Jul. 16, 2004.

* cited by examiner

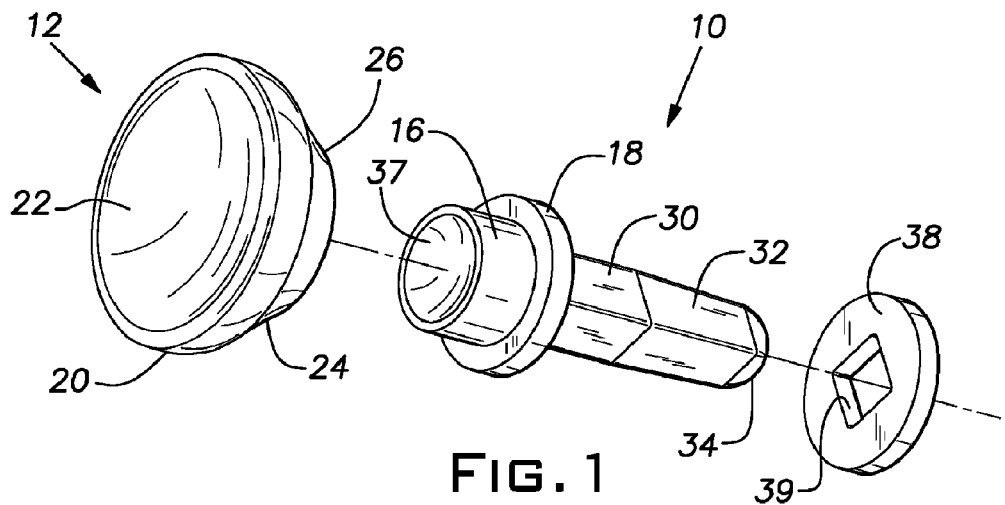
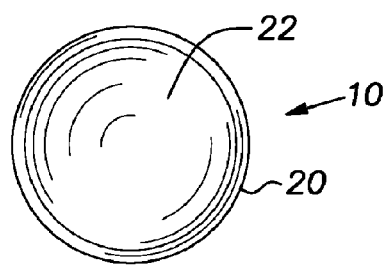
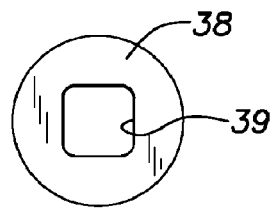
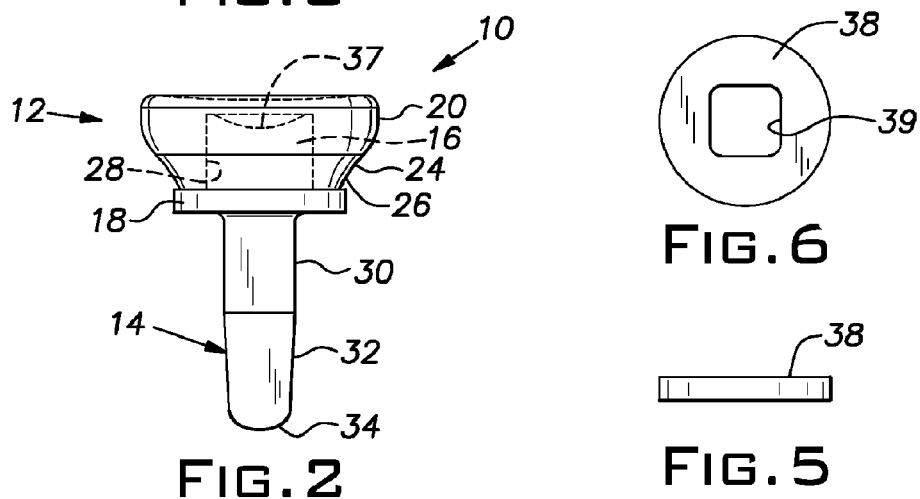
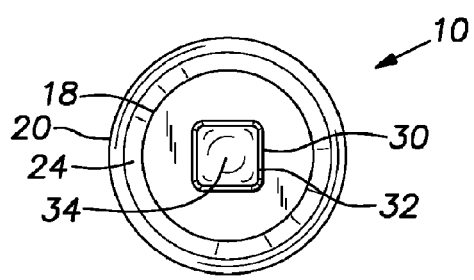

SMALL JOINT ORTHOPEDIC IMPLANTS AND THEIR MANUFACTURE

CROSS REFERENCE TO RELATED APPLICATION

This application claims priority to U.S. provisional application No. 60/607,473, entitled SMALL JOINT ORTHOPEDIC IMPLANTS AND THEIR MANUFACTURE, filed Sep. 3, 2004.

BACKGROUND OF THE INVENTION

1. Field of the Invention

The invention relates to small joint orthopedic implants and, more particularly, to a technique for the manufacture of such implants that is exceedingly efficient and which eliminates the need for a hospital or surgeon to acquire and maintain an inventory of such implants.

2. Description of the Prior Art

Current methods of small joint orthopedic implant manufacture involve the fabrication of a universal set of sizes of implants, which are sold or consigned to hospitals along with accompanying instrumentation. Because the implants are manufactured to pre-determined specifications, the surgical procedure necessarily requires that the patient's bone be configured to fit a standard implant. This procedure has a number of drawbacks.

For example, in the case of radial head (elbow joint) surgery, "monoblock" radial head metallic implants have evolved. Due to their size and rigidity, these "off-the-shelf" implants often require excessive bone resection to allow their insertion and are technically demanding to use. The difficulties associated with monoblock implants have led to the development of modular implants in which differently sized heads are fitted to differently sized stems. The heads usually are provided in a limited number of radial sizes, e.g., small, medium, and large. Unfortunately, as the length of the head increases, typically so does the diameter, and it is unlikely that any combination of modular parts will perfectly fit a given patient. A skilled surgeon can adapt such off-the-shelf implants to fit the anatomy of an acute fracture, but it is not uncommon that even in experienced hands an implant does not achieve a desired level of stability. With all of the referenced implants, it usually takes a great deal of time and skill on the part of the surgeon to properly prepare the bone so that it will receive the implant properly in order to produce a strong, reliable result.

One form of radial head implant is known as the Swanson titanium radial head implant and is commercially available from Wright Medical Technology of Arlington, Tenn. In this implant, ten sizes of stems are provided (five "regular" width and five "narrow" width) and five head sizes are provided. The implants are accompanied by a sizing set made of a non-sterile plastics material. In order to install the implant, the surgeon enlarges the intramedullary canal of the radius using a curette, rasp, or drill. Implants from the sizing set are used to determine which head and stem should be implanted. Thereafter, a titanium stem and head corresponding to those of the sizing set are installed. After installation, the stem and head are fixed relative to each other, i.e., there is no rotation of the head relative to the stem.

There are a number of techniques whereby implants are sized to fit a particular patient, but such techniques are exceedingly difficult and expensive to accomplish. Generally, such techniques are suitable only for manufacturing implants for large, complexly shaped joints such as the hip or knee joints. For example, U.S. Pat. No. 4,704,686 to Aldinger discloses a method of producing an "individually adjusted" endoprosthesis pin, the method including processing data of the bone density of the patient's bone at a number of points. Such bone density data are obtained by X-rays, tomography or nuclear spin resonance. These imaging techniques are also used to obtain dimensional measurements of the subject bone or joint and to fabricate the implant.

U.S. Pat. No. 4,936,862 to Walker, et al. discloses a method for making joint prostheses that is semi-standardized and semi-customized. A mathematical model of average joints and bones is developed from a statistically significant sample of the population. Images of the patient in question at the operative site are taken by tomography or radiography. Based on the actual patient data, an appropriate standard model bone/joint is chosen from the population sample. This model is modified appropriately to more closely match the patient in question. A computer-generated shape is modeled by CAD and fabricated by CAM and/or CNC to produce a prosthesis that closely approximates the patient's bone. This method is essentially a compromise, providing a virtually customized bone implant, but which avoids the difficulties and cost of attempting to determine the shape of the patient's bone, both internally and externally, by CAT scan and duplicating the bone.

U.S. Application Publication 2003/0120276 to Tallarida et al. discloses a method for measuring and mapping the articular surface of a patient's bone or joint, and fabricating a prosthesis based on these data. A fixation screw is drilled into a bone surface to provide a reference axis. A static post is inserted into the reference axis as a measuring tool. The joint is articulated around this axis, and this motion is recorded. The motion is mapped by feeding it into parametric engineering design software, which defines a three-dimensional surface, that is, patient-specific measurements. An implant is fabricated to match the contours of this three-dimensional surface. Preparation tools also can be fabricated using the same dimensions obtained through the mapping procedure. Hence, implant geometry and preparation tool geometry can be mated and optimized allowing an implant of minimum thickness and a minimal removal of bone matter. Other methods of mapping the intended surgical site and/or articular surface are contemplated, including MRI or CT scanning.

U.S. Pat. No. 5,002,579 to Copf et al. discloses a joint prosthesis and method for making the prosthesis. A small number of X-ray images are taken of the subject bone or joint, and the major contours of the bone are determined and stored in a computer. A computer is loaded with a pre-existing database of three-dimensional geometric data of various thighbones. The computer finds the bone data in the database most similar to the subject bone data gleaned from the X-ray images. These data are transferred and the details of the subject bone are interpolated therefrom. A model then is made that corresponds to a best-fit prosthesis suited for the subject bone. A computer program also is used to allocate support posts of the prosthesis along trabecular spicules in order that lines of force transmission through the prosthesis correspond to those in nature.

U.S. Pat. No. 5,522,900 to Hollister and U.S. Pat. No. 5,549,690 to Hollister et al. collectively disclose a generalized prosthetic joint and a prosthetic thumb joint, respectively, and methods for their manufacture. The method of manufacture begins with modeling the prosthetic joint by determining the two non-perpendicular and non-intersecting axes about which the joint rotates. Rotation about these axes produces the outline of a torus. Portions of this torus are then chosen which form ideal load-bearing surfaces of the prosthetic joint. An aspect of the inventions is to not only mimic the kinematics of a joint, but also to mimic the natural bony structure of the joint.

As will be apparent from the foregoing, there remains a need for a technique to manufacture small joint implants that avoids the need for a surgeon or hospital to maintain a large inventory of standardized implants. There also is a need for a technique to manufacture small joint orthopedic implants without incurring the time and expense needed to manufacture large, complexly shaped implants. Moreover, any such technique would produce an implant having the capability for the head to rotate relative to the stem, and for axial adjustments of the head relative to the bone to be made easily during installation. Yet additionally, any such technique would permit the implant to be installed quickly and accurately, while avoiding imprecise, difficult, and time-consuming preparation time.

SUMMARY OF THE INVENTION

In response to the foregoing considerations, the present invention provides a new and improved technique for the manufacture and installation of small joint orthopedic implants. The present invention also includes a new form of implant. The present invention is intended for use with various small joints, including, but not limited to, the radial head, ulnar head, basal thumb joint, great toe joint, and other finger and toe joints.

Pursuant to the method of the present invention, standard radiographs are taken of a pathologic joint and the corresponding non-pathologic joint. In order to provide an accurate frame of reference, a specialized marker is placed in the radiographic field. By inspection of the radiographs and by comparison with the marker, the dimensions of the bone, specifically the dimensions of the cortical bone and the cancellous bone, can be quickly and accurately determined. These dimensions can be used to manufacture a suitable implant, broach, and impact tool. In the preferred embodiment, the marker is a ball bearing of known dimensions that will provide an accurate frame of reference from any viewing angle.

Typically, the implant will include a stem from which a post projects. A radially extending collar is located at the intersection of the stem and the post. A mating head is attached to the post. The head closely approximates the size and shape of the natural head being replaced. The stem usually will be square, or at least non-round, in cross-section to prevent rotation of the stem in the bone, and will taper from a larger dimension adjacent the collar to a smaller dimension remote from the collar. For many applications, the head will not be fixedly attached to the post, but will be rotatable about the longitudinal axis of the post. The various design considerations for the implant will be described in more detail in the description that follows.

One or more spacers also can be provided for use by the surgeon. Each spacer is a disc having a thickness of 1.0 mm or 2.0 mm. The diameter of the spacer approximates that of the collar. The center of the spacer includes an opening of the same size and shape as the cross-section of the stem.

By referring to the radiographs, it will be possible to manufacture an implant that replicates the original bone. Preferably, however, the diameter of the head is slightly smaller than the original head. For example, in the case of radial head implants, the head typically is about 2.0 mm smaller than the original. This reduced size permits adequate capsular closure while attaining proper pronation and supination.

In order to install the implant, an osteotomy is performed on the defective head and neck to a predetermined point based on dimensions derived from the radiographs and instructions provided to the surgeon. A custom broach is made for each implant and is provided to the surgeon. The broach precisely duplicates the dimensions of the stem of the implant and conforms to the dimensions of the canal to be prepared. Consequently, the surgeon merely has to remove cancellous bone from the canal with the custom broach and the implant is ready for insertion. Guesswork and "overdone" canal preparation are eliminated. After the canal has been prepared, a custom-made impact tool is used to drive the stem into the canal until the collar engages the bone. The head is applied to the post and the tightness of the lateral fit is checked. If the fit is too tight, the implant is removed and additional bone is resected. If the fit is too loose, the implant is removed and an appropriate number and combination of spacers are fitted over the stem. After once again checking the fit, the surgical opening is closed.

The invention provides a technique to manufacture small joint orthopedic implants that avoids the need for a surgeon or hospital to maintain a large inventory of standardized implants. The invention also avoids complex procedures needed to manufacture large, complexly shaped implants. The implant has the capability for the head to rotate relative to the stem, and for axial adjustments of the head relative to the bone to be made easily during installation. Yet additionally, the surgical procedure can be accomplished much more quickly than prior procedures because no time is needed to select a properly sized implant, which frees the surgeon to concentrate only on installation of the implant.

The foregoing and other features of the invention will be apparent from the following description and claims.

BRIEF DESCRIPTION OF THE DRAWINGS

FIG. 1 is an exploded perspective view of an implant according to the invention;

FIG. 2 is a side elevation view of the implant of FIG. 1;

FIG. 3 is an end view of the implant of FIG. 1 showing a head portion of the implant;

FIG. 4 is an end view of the implant of FIG. 1 showing a stem portion of the implant;

FIG. 5 is a side elevation view of a spacer according to the invention;

FIG. 6 is an end view of the spacer of FIG. 5;

DESCRIPTION OF THE PREFERRED EMBODIMENT

Figure 7:
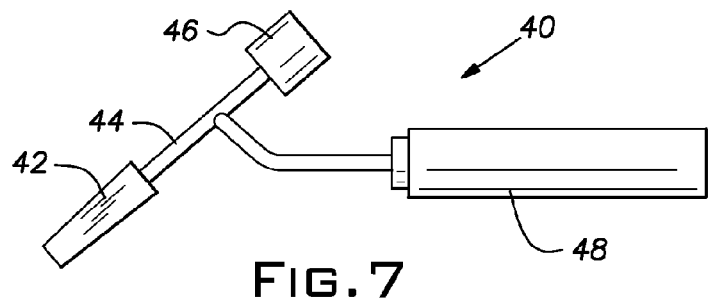
FIG. 7 is a side elevation view of an installation tool according to the invention.

Referring to FIGS. 1-4, an implant according to the invention is indicated generally by the reference numeral 10. The implant 10 as described herein is intended for radial head replacement, but it is to be understood that suitable modifications in size and shape as will be apparent to those skilled in the art will permit the implant 10 to be used for other types of small joints, such as ulnar head, basal thumb, and the like. It is expected that the implant 10 will be made of surgical grade stainless steel, although the use of other materials is possible.

The implant 10 includes a head 12 and a stem 14. A post 16 projects from the stem 14 along the longitudinal axis of the stem 14. A radially extending collar 18 is disposed at the intersection between the stem 14 and the post 16. The head 12 includes a generally cylindrical sidewall 20, a concave end face 22, a tapered portion 24 that tapers from a larger dimension at the intersection with the sidewall 20 to a smaller dimension at the end 26 of the head 12 remote from the end face 22. A cylindrical opening 28 is formed in the end 26. The outer diameter of the end 26 approximates that of the collar 18.

The stem 14 is non-round, preferably square, in cross-section. In the example given, the stem has a constant cross-section portion 30 that is adjacent to the collar 18. The length of the portion 30 is within the range of 4-7 mm, preferably 6 mm. The stem 14 has a tapered portion 32 that extends from the portion 30. The portion 32 tapers at an angle of about 3.0 degrees to a rounded end 34. In the example given, the stem 14 is about 17 mm long, although the exact length is a function of the patient's anatomy.

The collar 18 is about 2.0 mm thick. The diameter of the collar 18 is selected as a function of the patient's anatomy.

The post 16 is cylindrical with a concave end face 37. The post 16 fits within the opening 28. The fit between the post 16 and the opening 18 is such that the head 12 can rotate freely about the longitudinal axis of the post 16, but not so freely as to permit wobbling. In a typical example, the post 16 is about 0.235 inch long, has a diameter of about 0.353 inch, and the concave end face 37 has a radius of about 0.375 inch.

Referring now to FIGS. 5 and 6, a spacer 38 is illustrated. Preferably, a number of the spacers 38 are provided for use by the surgeon. Each spacer 38 has a thickness of either 1.0 mm or 2.0 mm. The outer diameter of each spacer 38 is the same as that of the collar 18. Each spacer 38 has a central aperture 39 that is the same size and shape as that of the portion 30.

Referring now to FIG. 7, an installation tool 40 is shown. The installation tool 40 is in the form of a broach that includes a rasp 42 that is the same size and shape as the stem 14. The installation tool 40 includes a shaft 44. The rasp 42 is attached to one end of the shaft 44 while an anvil 46 is attached to the other. A handle 48 is attached to the shaft 44 near its mid-point and extends away from the shaft 44 at an angle. It is expected that the manufacturer will maintain a quantity of installation tools 40 in stock while maintaining few or none of the rasps 42 in stock. The rasps 42 will be manufactured as the need arises and attached to the shaft 44.

Figure 8:
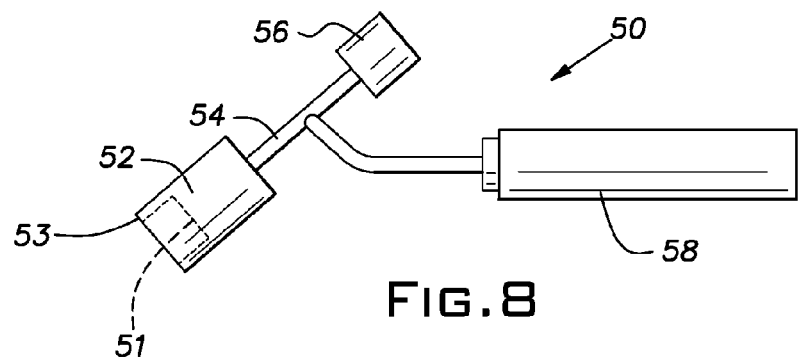
FIG. 8 is a side elevation view of an impact tool according to the invention.

Referring now to FIG. 8, an impact tool 50 is shown. The impact tool 50 includes a non-metallic head 52 made of a relatively soft material such as nylon that has an opening 51 that fits over the post 16 and an end face 53 that engages the collar 18. The impact tool 50 includes a shaft 54. The head 52 is attached to one end of the shaft 54 while an anvil 56 is attached to the other. A handle 58 is attached to the shaft 54 near its mid-point and extends away from the shaft 54 at an angle. It is expected that the manufacturer will maintain a quantity of impact tools 50 in stock while maintaining few or none of the heads 52 in stock. The heads 52 will be manufactured as the need arises and attached to the shaft 54.

Manufacture of the Implant 10

Figure 9:
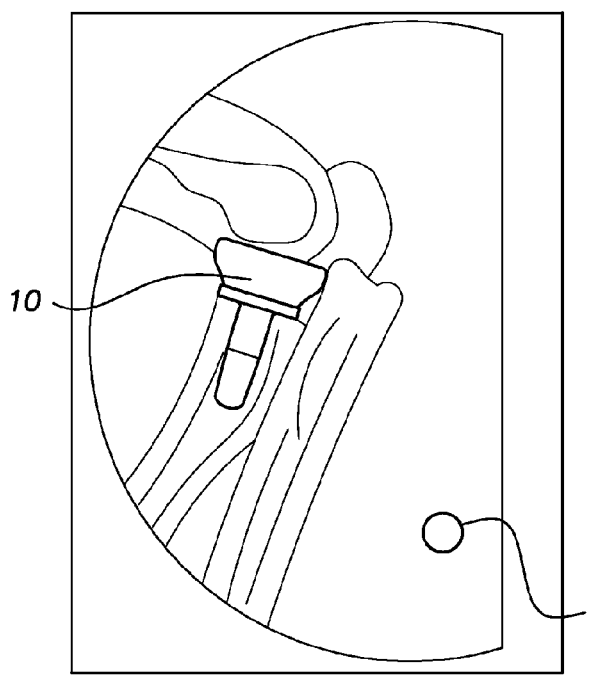
FIG. 9 is a lateral radiograph of an implant according to the invention installed in a patient's elbow and showing the image of a marker used to manufacture the implant.

The present invention involves the custom manufacture of the implant 10 to fit a particular patient, as well as the custom manufacture of the installation tool 40 and the impact tool 50. The following steps are performed:

1. Radiographs are taken of the affected joint of the patient. The only radiographs of the affected joint that are necessary are the conventional AP (anteroposterior) and lateral projections. In order to provide a scale for the radiographs, a marker 60 (FIG. 9) is placed in the field of the radiograph. Preferably, the marker 60 is placed close to a plane within which the centerline of the bone lies. In the preferred embodiment, the marker 60 is a steel ball bearing having a known diameter of about 25.4 mm (1.0 inch). Because the marker 60 is spherical, accurate measurements can be made from any viewing angle.

2. Radiographs as in the preceding step are taken of the non-pathologic joint of the patient for comparison purposes and to generate an anatomic fit.

3. The location that an osteotomy is to be performed is determined. In the usual case, the osteotomy should be made approximately 1.0 mm below, or distally of, the defective bone.

4. The outer diameter of the bone at the expected osteotomy site is determined.

5. The width of the intramedullary canal is determined by using line-to-line dimensions from inside the medial cortical bone to inside the lateral cortical bone. This measurement is taken 2.0-4.0 mm below the expected osteotomy site.

6. The location of the radial tuberosity is determined.

7. The implant 10 is manufactured, usually by machining, using data from the following matrices. The information contained in the matrices provides preferred proportional relations for the various possible dimensions of the implant 10.

Custom Radial Head Dimension Matrix for Implant Sizing

| (Height of head vs. diameter of head, in millimeters) | | | | | | | | | | | | | | | | | | | | | | | | | | |
|---|---|---|---|---|---|---|---|---|---|---|---|---|---|---|---|---|---|---|---|---|---|---|---|---|---|---|
| H | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
| 6 | 6 | 6 | 6 | 6 | 6 | 6 | | | | | | | | | | | | | | | | | | | | |
| 7 | 7 | 7 | 7 | 7 | 7 | 7 | 7 | 7 | 7 | | | | | | | | | | | | | | | | | |
| 8 | 8 | 8 | 8 | 8 | 8 | 8 | 8 | 8 | | | 8 | 8 | 8 | 8 | 8 | 8 | | | | | | | | | | |
| 9 | 9 | 9 | 9 | 9 | 9 | 9 | 9 | 9 | 9 | 9 | 9 | 9 | 9 | 9 | 9 | 9 | | | | | | | | | | |
| 10 | 10 | 10 | 10 | 10 | 10 | 10 | 10 | 10 | 10 | 10 | 10 | 10 | 10 | 10 | 10 | 10 | | | | | | | | | | |
| 11 | 11 | 11 | 11 | 11 | 11 | 11 | 11 | 11 | 11 | 11 | 11 | 11 | 11 | 11 | 11 | 11 | | | | | | | | | | |
| 12 | | | | | | | 12 | 12 | 12 | 12 | 12 | 12 | 12 | 12 | 12 | 12 | | | | | | | | | | |
| 13 | | | | | | | 13 | 13 | 13 | 13 | 13 | 13 | 13 | 13 | 13 | 13 | | | | | | | | | | |
| 14 | | | | | | | 14 | 14 | 14 | 14 | 14 | 14 | 14 | 14 | 14 | 14 | 14 | 14 | 14 | 14 | 14 | 14 | 14 | 14 | 14 | 14 |
| 15 | | | | | | | 15 | 15 | 15 | 15 | 15 | 15 | 15 | 15 | 15 | 15 | 15 | 15 | 15 | 15 | 15 | 15 | 15 | 15 | 15 | 15 |
| 16 | | | | | | | | 16 | 16 | 16 | 16 | 16 | 16 | 16 | 16 | 16 | 16 | 16 | 16 | 16 | 16 | 16 | 16 | 16 | 16 | 16 |
| 17 | | | | | | | | 17 | 17 | 17 | 17 | 17 | 17 | 17 | 17 | 17 | 17 | 17 | 17 | 17 | 17 | 17 | 17 | 17 | 17 | 17 |
| 18 | | | | | | | | 18 | 18 | 18 | 18 | 18 | 18 | 18 | 18 | 18 | 18 | 18 | 18 | 18 | 18 | 18 | 18 | 18 | 18 | 18 |
| 19 | | | | | | | | | | | | | | | | | | 19 | 19 | 19 | 19 | 19 | 19 | 19 | 19 | 19 |
| 20 | | | | | | | | | | | | | | | | | | 20 | 20 | 20 | 20 | 20 | 20 | 20 | 20 | 20 |
| 21 | | | | | | | | | | | | | | | | | | 21 | 21 | 21 | 21 | 21 | 21 | 21 | 21 | 21 |

-continued (Height of head vs. diameter of head, in millimeters)

| H | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|
| 22 | | | | | | | | | | | | | | | | | 22 | 22 | 22 | 22 | 22 | 22 | 22 | 22 | 22 | 22 |
| 23 | | | | | | | | | | | | | | | | | 23 | 23 | 23 | 23 | 23 | 23 | 23 | 23 | 23 | 23 |
| 24 | | | | | | | | | | | | | | | | | 24 | 24 | 24 | 24 | 24 | 24 | 24 | 24 | 24 | 24 |

Custom Radial Stem Implant Sizing Matrix (Length of stem vs. width of stem, in millimeters)

| L | 4 | 4.5 | 5 | 5.5 | 6 | 6.5 | 7 | 7.5 | 8 | 8.5 | 9 | 9.5 | 10 | 10.5 | 11 | 11.5 | 12 | 12.5 | 13 | 13.5 | 14 | 14.5 | 15 | 15.5 |
|---|---|---|---|---|---|---|---|---|---|---|---|---|---|---|---|---|---|---|---|---|---|---|---|---|
| 15 | 15 | 15 | 15 | 15 | 15 | 15 | | | | | | | | | | | | | | | | | | |
| 16 | 16 | 16 | 16 | 16 | 16 | 16 | | | | | | | | | | | | | | | | | | |
| 17 | 17 | 17 | 17 | 17 | 17 | 17 | | | | | | | | | | | | | | | | | | |
| 18 | 18 | 18 | 18 | 18 | 18 | 18 | | | | | | | | | | | | | | | | | | |
| 19 | 19 | 19 | 19 | 19 | 19 | 19 | | | | | | | | | | | | | | | | | | |
| 20 | 20 | 20 | 20 | 20 | 20 | 20 | | | | | | | | | | | | | | | | | | |
| 21 | 21 | 21 | 21 | 21 | 21 | 21 | 21 | 21 | 21 | 21 | 21 | 21 | 21 | 21 | 21 | 21 | | | | | | | | |
| 22 | 22 | 22 | 21 | 21 | 21 | 21 | 22 | 22 | 22 | 22 | 22 | 22 | 22 | 22 | 22 | 22 | | | | | | | | |
| 23 | 23 | 23 | 23 | 23 | 23 | 23 | 23 | 23 | 23 | 23 | 23 | 23 | 23 | 23 | 23 | 23 | | | | | | | | |
| 24 | 24 | 24 | 24 | 24 | 24 | 24 | 24 | 24 | 24 | 24 | 24 | 24 | 24 | 24 | 24 | 24 | | | | | | | | |
| 25 | | | | | | | 25 | 25 | 25 | 25 | 25 | 25 | 25 | 25 | 25 | 25 | | | | | | | | |
| 26 | | | | | | | 26 | 26 | 26 | 26 | 26 | 26 | 26 | 26 | 26 | 26 | | | | | | | | |
| 27 | | | | | | | 27 | 27 | 27 | 27 | 27 | 27 | 27 | 27 | 27 | 27 | | | | | | | | |
| 28 | | | | | | | 28 | 28 | 28 | 28 | 28 | 28 | 28 | 28 | 28 | 28 | 28 | 28 | 28 | 28 | 28 | 28 | 28 | 28 |
| 29 | | | | | | | 29 | 29 | 29 | 29 | 29 | 29 | 29 | 29 | 29 | 29 | 29 | 29 | 29 | 29 | 29 | 29 | 29 | 29 |
| 30 | | | | | | | 30 | 30 | 30 | 30 | 30 | 30 | 30 | 30 | 30 | 30 | 30 | 30 | 30 | 30 | 30 | 30 | 30 | 30 |
| 31 | | | | | | | | | | | | | | | | | 31 | 31 | 31 | 31 | 31 | 31 | 31 | 31 |
| 32 | | | | | | | | | | | | | | | | | 32 | 32 | 32 | 32 | 32 | 32 | 32 | 32 |
| 33 | | | | | | | | | | | | | | | | | 33 | 33 | 33 | 33 | 33 | 33 | 33 | 33 |
| 34 | | | | | | | | | | | | | | | | | 34 | 34 | 34 | 34 | 34 | 34 | 34 | 34 |
| 35 | | | | | | | | | | | | | | | | | 35 | 35 | 35 | 35 | 35 | 35 | 35 | 35 |
| 36 | | | | | | | | | | | | | | | | | 36 | 36 | 36 | 36 | 36 | 36 | 36 | 36 |
| 37 | | | | | | | | | | | | | | | | | 37 | 37 | 37 | 37 | 37 | 37 | 37 | 37 |
| 38 | | | | | | | | | | | | | | | | | 38 | 38 | 38 | 38 | 38 | 38 | 38 | 38 |
| 39 | | | | | | | | | | | | | | | | | 39 | 39 | 39 | 39 | 39 | 39 | 39 | 39 |
| 40 | | | | | | | | | | | | | | | | | 40 | 40 | 40 | 40 | 40 | 40 | 40 | 40 |
| 41 | | | | | | | | | | | | | | | | | 41 | 41 | 41 | 41 | 41 | 41 | 41 | 41 |
| 42 | | | | | | | | | | | | | | | | | 42 | 42 | 42 | 42 | 42 | 42 | 42 | 42 |
| 43 | | | | | | | | | | | | | | | | | 43 | 43 | 43 | 43 | 43 | 43 | 43 | 43 |

Figure 10:
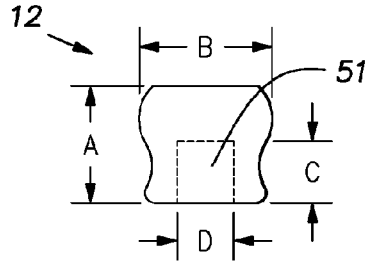
FIG. 10 illustrates dimensions to be used in conjunction with the table herein entitled, "Ulnar Head Dimension"

Ulnar Head Dimension (to be Used in Conjunction with FIG. 10)

[1] "C" FIG. 10 is approximately 0.275+0.001 mm. "D" in FIG. 10 is approximately 0.257+0.001 mm.

("A" Dimension Head Height vs. "B" Dimension Head Diameter, in millimeters)

| A | | | | | | | | | | | | | | | | | |
|---|---|---|---|---|---|---|---|---|---|---|---|---|---|---|---|---|---|
| 10 | 10 | 11 | 12 | 12.5 | 13 | 13.5 | 14.5 | 15 | 15.5 | 16 | 16.5 | 17 | 17.5 | 18 | 18.5 | 19 | 20 |
| 10.5 | 10 | 11 | 12 | 12.5 | 13 | 13.5 | 14.5 | 15 | 15.5 | 16 | 16.5 | 17 | 17.5 | 18 | 18.5 | 19 | 20 |
| 11 | 10 | 11 | 12 | 12.5 | 13 | 13.5 | 14.5 | 15 | 15.5 | 16 | 16.5 | 17 | 17.5 | 18 | 18.5 | 19 | 20 |
| 11.5 | 10 | 11 | 12 | 12.5 | 13 | 13.5 | 14.5 | 15 | 15.5 | 16 | 16.5 | 17 | 17.5 | 18 | 18.5 | 19 | 20 |
| 12 | 10 | 11 | 12 | 12.5 | 13 | 13.5 | 14.5 | 15 | 15.5 | 16 | 16.5 | 17 | 17.5 | 18 | 18.5 | 19 | 20 |
| 12.5 | 10 | 11 | 12 | 12.5 | 13 | 13.5 | 14.5 | 15 | 15.5 | 16 | 16.5 | 17 | 17.5 | 18 | 18.5 | 19 | 20 |
| 13 | 10 | 11 | 12 | 12.5 | 13 | 13.5 | 14.5 | 15 | 15.5 | 16 | 16.5 | 17 | 17.5 | 18 | 18.5 | 19 | 20 |
| 13.5 | 10 | 11 | 12 | 12.5 | 13 | 13.5 | 14.5 | 15 | 15.5 | 16 | 16.5 | 17 | 17.5 | 18 | 18.5 | 19 | 20 |
| 14 | 10 | 11 | 12 | 12.5 | 13 | 13.5 | 14.5 | 15 | 15.5 | 16 | 16.5 | 17 | 17.5 | 18 | 18.5 | 19 | 20 |
| 14.5 | 10 | 11 | 12 | 12.5 | 13 | 13.5 | 14.5 | 15 | 15.5 | 16 | 16.5 | 17 | 17.5 | 18 | 18.5 | 19 | 20 |
| 15 | 10 | 11 | 12 | 12.5 | 13 | 13.5 | 14.5 | 15 | 15.5 | 16 | 16.5 | 17 | 17.5 | 18 | 18.5 | 19 | 20 |
| 15.5 | 10 | 11 | 12 | 12.5 | 13 | 13.5 | 14.5 | 15 | 15.5 | 16 | 16.5 | 17 | 17.5 | 18 | 18.5 | 19 | 20 |
| 16 | 10 | 11 | 12 | 12.5 | 13 | 13.5 | 14.5 | 15 | 15.5 | 16 | 16.5 | 17 | 17.5 | 18 | 18.5 | 19 | 20 |
| 16.5 | 10 | 11 | 12 | 12.5 | 13 | 13.5 | 14.5 | 15 | 15.5 | 16 | 16.5 | 17 | 17.5 | 18 | 18.5 | 19 | 20 |
| 17 | 10 | 11 | 12 | 12.5 | 13 | 13.5 | 14.5 | 15 | 15.5 | 16 | 16.5 | 17 | 17.5 | 18 | 18.5 | 19 | 20 |
| 17.5 | 10 | 11 | 12 | 12.5 | 13 | 13.5 | 14.5 | 15 | 15.5 | 16 | 16.5 | 17 | 17.5 | 18 | 18.5 | 19 | 20 |
| 18 | 10 | 11 | 12 | 12.5 | 13 | 13.5 | 14.5 | 15 | 15.5 | 16 | 16.5 | 17 | 17.5 | 18 | 18.5 | 19 | 20 |
| 18.5 | 10 | 11 | 12 | 12.5 | 13 | 13.5 | 14.5 | 15 | 15.5 | 16 | 16.5 | 17 | 17.5 | 18 | 18.5 | 19 | 20 |

("A" Dimension Head Height vs. "B" Dimension Head Diameter, in millimeters)

A

| 19   | 10 | 11 | 12 | 12.5 | 13 | 13.5 | 14.5 | 15 | 15.5 | 16 | 16.5 | 17 | 17.5 | 18 | 18.5 | 19 | 20 |
|------|----|----|----|------|----|------|------|----|------|----|------|----|------|----|------|----|----|
| 19.5 | 10 | 11 | 12 | 12.5 | 13 | 13.5 | 14.5 | 15 | 15.5 | 16 | 16.5 | 17 | 17.5 | 18 | 18.5 | 19 | 20 |
| 20   | 10 | 11 | 12 | 12.5 | 13 | 13.5 | 14.5 | 15 | 15.5 | 16 | 16.5 | 17 | 17.5 | 18 | 18.5 | 19 | 20 |

Figure 11:
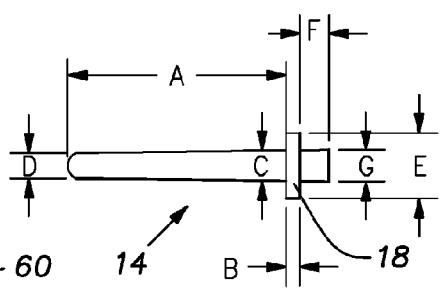
FIG. 11 illustrates dimensions to be used in conjunction with the table herein entitled, "Ulnar Stem Dimension."

Ulnar Stem Dimension (to be Used in Conjunction with FIG. 11)

[2]"F" in FIG. 11 is approximately 0.256±0.001 mm. "G" in FIG. 11 is approximately 0.256+0.0005 mm to 0.256-0.0010 mm.

(Length of stem vs. width of stem, in millimeters)

| MM | "B" Range | "C" Range | "D" Range | "E" Range |
|----|-----------|-----------|-----------|-----------|
| 40 | 2 mm-30 mm | 5.5 mm-9.0 mm | 4.0 mm-8.0 mm | 8.0 mm-12.0 mm |
| 42 | 2 mm-30 mm | 5.5 mm-9.0 mm | 4.0 mm-8.0 mm | 8.0 mm-12.0 mm |
| 44 | 2 mm-30 mm | 5.5 mm-9.0 mm | 4.0 mm-8.0 mm | 8.0 mm-12.0 mm |
| 46 | 2 mm-30 mm | 5.5 mm-9.0 mm | 4.0 mm-8.0 mm | 8.0 mm-12.0 mm |
| 47 | 2 mm-30 mm | 5.5 mm-9.0 mm | 4.0 mm-8.0 mm | 8.0 mm-12.0 mm |
| 48 | 2 mm-30 mm | 5.5 mm-9.0 mm | 4.0 mm-8.0 mm | 8.0 mm-12.0 mm |
| 49 | 2 mm-30 mm | 5.5 mm-9.0 mm | 4.0 mm-8.0 mm | 8.0 mm-12.0 mm |
| 50 | 2 mm-30 mm | 5.5 mm-9.0 mm | 4.0 mm-8.0 mm | 8.0 mm-12.0 mm |
| 51 | 2 mm-30 mm | 5.5 mm-9.0 mm | 4.0 mm-8.0 mm | 8.0 mm-12.0 mm |
| 52 | 2 mm-30 mm | 5.5 mm-9.0 mm | 4.0 mm-8.0 mm | 8.0 mm-12.0 mm |
| 53 | 2 mm-30 mm | 5.5 mm-9.0 mm | 4.0 mm-8.0 mm | 8.0 mm-12.0 mm |
| 54 | 2 mm-30 mm | 5.5 mm-9.0 mm | 4.0 mm-8.0 mm | 8.0 mm-12.0 mm |
| 55 | 2 mm-30 mm | 5.5 mm-9.0 mm | 4.0 mm-8.0 mm | 8.0 mm-12.0 mm |
| 56 | 2 mm-30 mm | 5.5 mm-9.0 mm | 4.0 mm-8.0 mm | 8.0 mm-12.0 mm |
| 58 | 2 mm-30 mm | 5.5 mm-9.0 mm | 4.0 mm-8.0 mm | 8.0 mm-12.0 mm |
| 60 | 2 mm-30 mm | 5.5 mm-9.0 mm | 4.0 mm-8.0 mm | 8.0 mm-12.0 mm |

8. Typical dimensions for an implant 10 according to the invention are as follows:

a. The outer diameter of the collar 18 approximates that of the bone at the expected osteotomy site.

b. The cross-section of stem 14 is constant for 4.0-7.0 mm, preferably 6.0 mm, below the collar 18. In the usual case the cross-section is square.

c. The diagonal width of the stem 14 adjacent the collar 18 is the same as the width of the intramedullary canal at a location 2.0-4.0 mm below the expected osteotomy site.

d. Below the constant cross-section portion of the stem 14, the stem 14 tapers at an angle of 3.0 degrees.

e. The overall length of the stem 14 is about 17.0 mm, but in no case does it extend past the radial tuberosity.

f. The collar 18 is about 2.0 mm thick.

g. The post 16 is about 6.0 mm long with diameter of about 9.0 mm.

h. The end of the post 16 is concave with a radius approximating that of the natural head.

i. The head 12 replicates the natural head but with a slightly smaller outer diameter (about 2 mm smaller). Typically, the maximum outer diameter of the head 12 is about 21.0 mm and the height of the head 12 is about 11.5 mm.

9. The spacers 38 are manufactured.

10. The rasp 42 is made to the dimensions of the stem 14.

11. The head 52 is made to the dimensions of the post 16 and the collar 18.

After suitable radiographs have been received from the surgeon, engineering drawings can be prepared using the steps identified above. The implant 10, spacers, 38, installation tool (broach) 40, and impact tool 50 then are fabricated in accordance with the drawings. The foregoing components are packed in a sterilization tray and are shipped to the surgeon or hospital. The manufacturing process can be accomplished in a short time, usually on the order of three to seven days after receipt of radiographs from the surgeon. Because implant surgery rarely needs to be accomplished on an emergency basis, and indeed often is delayed to permit swelling to subside, the small delay experienced by the patient and surgeon in receiving the implant does not adversely affect the quality of the implant procedure. Moreover, the resulting product is far superior to existing standardized implants.

Installation of the Implant 10

Installation of the implant 10 will be described in the contest of radial head replacement. Appropriate installation procedures for other types of implant surgery will be apparent to those skilled in the art.

Indications for use of the radial head implant 10 include radial head fracture not amenable to fixation, radio capitellar arthropathy due to degeneration or malunion of a radial head fracture, complex fracture dislocation of the elbow with loss of radial head support and Essex-Lopresti fracture-dislocation with loss of the radial head, rupture of the interosseous membrane and disruption of the distal radio-ulnar joint. After the implant 10 has been manufactured pursuant to the previously described instructions, the following steps are performed:

1. The surgical technique uses a direct lateral approach through the extesor digitorum communis muscle. The joint capsule and the orbicular ligament are opened longitudinally.

2. The radial head and neck are visualized, and an oscillating saw is used to resect the radial head to a predetermined level based on radiograph study.

3. The intramedullary canal is prepared using the customized rasp 42. The rasp 42 conforms anatomically to the stem 14 and hence to the patient's canal, allowing optimal preparation of the canal with minimal removal of osseous and marrow tissue.

4. After the canal has been broached, the stem 14 is inserted and impacted with the impact tool 50 until the collar 18 is fully seated on the radial neck.

5. The head 12 then is applied to the post 16.

6. The now-installed implant 10 can be checked for tightness of fit. If the fit is too tight, the implant 10 is removed, and an incremental broaching or resection may be performed. If the fit is too loose to provide adequate lateral stability, one or more of the spacers 38 are applied over the stem 14 in order to make the head 12 project further from the bone.

7. After the implant 10 is well inserted and lateral stability has been achieved, full pronation and supination are also checked and confirmed.

8. The joint capsule is closed with a running suture, which in the preferred embodiment is 3.0 non-absorbable braided polyester. The muscle fascia is approximated over the capsule-closing suture with a running simple suture, which in the preferred embodiment is 2.0 or 3.0 braided polyester. The skin then is closed with an absorbable subcuticular running suture.

As will be apparent from the foregoing description, the invention provides a technique to manufacture small joint orthopedic implants that avoids the need for a surgeon or hospital to maintain a large inventory of standardized implants. The invention also avoids the time and expense needed to manufacture large, complexly shaped implants. The implant according to the invention is superior to prior implants because it is precisely manufactured to each patient's individual requirements. The implant has the capability for the head to rotate relative to the stem, and for axial adjustments of the head relative to the bone to be made easily during installation. In part due to the custom-designed installation tool, the implant can be installed quickly and accurately, while avoiding imprecise, difficult, and time-consuming preparation time.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

In the manufacture of small joint orthopedic implants standard radiographs of a pathologic joint and the corresponding non-pathologic joint are taken. A specialized marker is placed in the radiographic field. By inspection of the radiographs and by comparison with the marker, the dimensions of the cortical bone and the cancellous bone can be determined and used to manufacture a suitable implant and installation tool. Typically, the implant has a stem from which a post projects. A radially extending collar is located at the intersection between the stem and the post. A mating head is attached to the post. For many applications, the head will be rotatable about the longitudinal axis of the post. One or more spacers that fit about the stem can be provided in order to adjust the distance that the head projects from the bone.

What is claimed is:

1. A method for manufacturing a small joint orthopedic implant, comprising the steps of:
    obtaining one or more first radiographs of a pathologic joint of a patient for which the implant is to be manufactured, the first radiographs including a marker of known dimensions;
    obtaining one or more second radiographs of the corresponding non-pathologic joint of the patient, the second radiographs including a marker of known dimensions;
    determining the location where an osteotomy should be performed on the pathologic joint by using the first and second radiographs;
    determining the dimensions of the cortical bone into which the implant is to be inserted in the region of the osteotomy by using the first and second radiographs; and
    fabricating the implant to conform to the dimensions of the cortical bone in the region of the osteotomy.

2. The method of claim 1, further comprising the step of providing an installation tool for removing cancellous bone in the region of the osteotomy, the installation tool having dimensions the same as those of the implant.

3. The method of claim 2, wherein the installation tool is a broach having a rasp end.

4. The method of claim 3, further comprising the step of providing an impact tool for driving the implant into the bone at the site of the osteotomy.

5. The method of claim 4, wherein that portion of the impact tool that comes in contact with implant has dimensions the same as those of the implant.

6. The method of claim 1, wherein the implant includes a collar having first and second opposing sides, a stem that projects from one side of the collar and which extends into the bone at the site of the osteotomy, a post that projects from the other side of the collar, and a head that is connected to the post.

7. The method of claim 6, wherein:
    the stem defines a longitudinal axis and in non-round in cross section;
    the post defines a longitudinal axis and is circular in cross section; and
    the head is connected to the post such that it can rotate about the longitudinal axis of the post.

8. The method of claim 6, further comprising the step of providing a plurality of disc-like spacers, each spacer having a central opening of the same size and shape as the cross-section of the stem in the region of the collar.

9. The method of claim 1, wherein the first and second radiographs are received from a surgeon or hospital located at a facility separate from a manufacturing facility where the implant is manufactured, and further comprising the steps of:
    manufacturing the implant at the manufacturing facility upon receipt of the first and second radiographs from the surgeon or hospital; and
    shipping the implant to the surgeon or hospital immediately upon manufacture.

10. The method of claim 1, wherein the implant is for joints in body locations selected from the group consisting of elbow, wrist, hand, ankle, and foot.

11. The method of claim 1, wherein the marker used in the first and second radiographs is spherical.

12. A method for manufacturing a small joint orthopedic implant for bones located in elbow, wrist, hand, ankle, or foot, comprising the steps of:
    obtaining one or more first radiographs of a pathologic joint of a patient for which the implant is to be manufactured, the first radiographs including a marker of known dimensions;
    obtaining one or more second radiographs of the corresponding non-pathologic joint of the patient, the second radiographs including a marker of known dimensions, the first and second radiographs being received from a surgeon or hospital located at a facility separate from a manufacturing facility where the implant is to be manufactured;
    determining the location where an osteotomy should be performed on the pathologic joint by using the first and second radiographs;
    determining the dimensions of the cortical bone into which the implant is to be inserted in the region of the osteotomy by using the first and second radiographs; and
    fabricating the implant to conform to the dimensions of the cortical bone in the region of the osteotomy, the implant including a stem that extends into the bone at the site of the osteotomy and a head that is connected to the stem, the stem defining a longitudinal axis and being non-round in cross-section, the head being connected to the stem such that it can rotate about the longitudinal axis of the stem;
    providing an installation tool in the form of a broach having a rasp end for removing the cancellous bone in the region of the osteotomy, the installation tool having dimensions the same as those of the implant;
    providing an impact tool for driving the implant into the bone at the site of the osteotomy, that portion of the impact tool that comes in contact with the implant having dimensions the same as those of the implant;

manufacturing the implant at the manufacturing facility upon receipt of the first and second radiographs from the surgeon or hospital; and shipping the implant to the surgeon or hospital immediately upon manufacture.

13. The method of claim 12, wherein the marker used in the first and second radiographs is spherical.

14. A small joint orthopedic implant for insertion into the intramedullary canal of a bone upon which an osteotomy has been performed, comprising:

a collar having first and second opposing sides;

a stem connected to the first side of the collar and extending therefrom along a longitudinal axis, the stem adapted to extend into the intramedullary canal of a patient's bone, the stem being non-round in cross-section and having a first section with a constant cross-section extending from the collar for a distance within the range of about 4-7 mm from the collar, the stem further having a second section extending from the first section and tapering to a smaller dimension at an angle of about three degrees relative to the longitudinal axis of the stem;

a post connected to the second side of the collar and extending therefrom along a longitudinal axis; and a head connected to the post, the head approximating the size and shape of the patient's original bone and being rotatable about the longitudinal axis of the post.

15. The implant of claim 14, wherein the stem is square in cross-section.

16. The implant of claim 14, wherein the post is cylindrical.

17. The implant of claim 14, wherein the collar has an outer diameter that approximates the outer diameter of the bone at the site of the osteotomy.

18. The implant of claim 14, further comprising a plurality of disc spacers, each spacer having a central opening of the same size and shape as the cross-section of the first section of the stem.

19. A small joint orthopedic implant for insertion into the intramedullary canal of a bone upon which an osteotomy has been performed, comprising: a collar having first and second opposing sides; a stem connected to the first side of the collar and extending therefrom along a longitudinal axis, the stem adapted to extend into the intramedullary canal of a patient's bone, the stem being non-round in cross-section and defining a first section and a second section tapering and extending from the first section; a post connected to the second side of the collar and extending therefrom along a longitudinal axis; and a head connected to the post, the head approximating the size and shape of the patient's original bone and being rotatable about the longitudinal axis of the post, further comprising a plurality of spacers, each spacer having a central opening of the same size and shape as the cross-section of the first section of the stem.

20. The implant of claim 19, wherein the first section of the stem has a constant cross-section extending from the collar for a distance within the range of about 4-7 mm from the collar.

21. The implant of claim 19, wherein the second section of the stem tapers to a smaller dimension at an angle of about three degrees relative to the longitudinal axis.

22. A small joint orthopedic implant for insertion into the intramedullary canal of a bone upon which an osteotomy has been performed, comprising:

a collar having first and second opposing sides, the collar having an outer diameter that approximates the outer diameter of the bone at the site of the osteotomy;

a stem connected to the first side of the collar and extending therefrom along a longitudinal axis, the stem adapted to extend into the intramedullary canal of a patient's bone, the stem being square in cross-section and having a first section with a constant cross-section extending from the collar for a distance within the range of about 4-7 mm from the collar, the stem further having a second section extending from the first section and tapering to a smaller dimension at an angle of about three degrees relative to the longitudinal axis of the stem;

a cylindrical post connected to the second side of the collar and extending therefrom along a longitudinal axis;

a head connected to the post, the head approximating the size and shape of the patient's original bone and being rotatable about the longitudinal axis of the post; and a plurality of disc spacers, each spacer having a central opening of the same size and shape as the cross-section of the first section of the stem.

* * * * *